United States Patent
Matsui et al.

(10) Patent No.: US 7,598,358 B2
(45) Date of Patent: Oct. 6, 2009

(54) METAL COMPLEX OF HETEROCYCLIC AROMATIC COMPOUND

(75) Inventors: Eriko Matsui, Kanagawa (JP); Yuriko Kaino, Kanagawa (JP); Toshiyuki Kunikiyo, Kanagawa (JP); Tatsushiro Hirata, Kanagawa (JP); Yoshifumi Mori, Chiba (JP)

(73) Assignee: Sony Corporation, Tokyo (JP)

( * ) Notice: Subject to any disclaimer, the term of this patent is extended or adjusted under 35 U.S.C. 154(b) by 438 days.

(21) Appl. No.: 11/368,793

(22) Filed: Mar. 6, 2006

(65) Prior Publication Data

US 2006/0145151 A1 Jul. 6, 2006

Related U.S. Application Data

(63) Continuation of application No. 10/468,982, filed as application No. PCT/JP02/13228 on Dec. 18, 2002, now Pat. No. 7,038,025.

(30) Foreign Application Priority Data

Dec. 27, 2001 (JP) ............................ 2001-396451

(51) Int. Cl.
  *C09B 45/00* (2006.01)
(52) U.S. Cl. ...................... 534/692; 548/541
(58) Field of Classification Search ................. 534/692; 548/541
  See application file for complete search history.

(56) References Cited

U.S. PATENT DOCUMENTS 5,545,308 A   8/1996  Murphy et al.

7,038,025 B2 *  5/2006  Matsui et al. ............... 534/692

OTHER PUBLICATIONS

Norman P. et al: "Two-photon absorption in five-membered heteroaromatic oligomers" Optics Communications, North-Holland Publishing Co. Amsterdam, NL, vol. 168, No. 1-4, Sep. 1, 1999, pp. 297-303, XP004179301 ISSN: 0030-4018.

Choi et al.: "Theoretical study of the nonlinear optical properties of thiophene, furan, pyrrole, (1,2,4-triazole), (1,3,4-oxadiazole), and (1,3,4-thiadiazole) monomers and obligomers" Bulletin of the Korean Chemical Society, vol. 19, No. 3, 1998, pp. 299-307, XP002323983.

* cited by examiner

*Primary Examiner*—Rei-tsang Shiao
(74) *Attorney, Agent, or Firm*—Frommer Lawrence & Haug LLP; William S. Frommer

(57) ABSTRACT

A novel metal complex of a heterocyclic aromatic compound which shows a low activation energy, is stabilized structurally, is capable of modulation of the structure thereof, and capable of preferably functioning as a molecular device in technological fields. The metal complex of a heterocyclic aromatic compound comprises a transition metal (for example, silver ion) as a central atom, and basic ligands comprised of a 5-membered heterocyclic aromatic compound (for example, pyrrole rings), in which the position of the central atom can be changed by an internal factor such as transfer of an electric charge or by an external factor such as application of an electric field, a change in acidity of the surrounding environment, etc., whereby the number of atoms (or the number of electrons) relating to the coordination ability can be modulated, and, upon polymerization, the conformation can be modulated depending on the position of the central atom.

12 Claims, 14 Drawing Sheets

F I G. 5
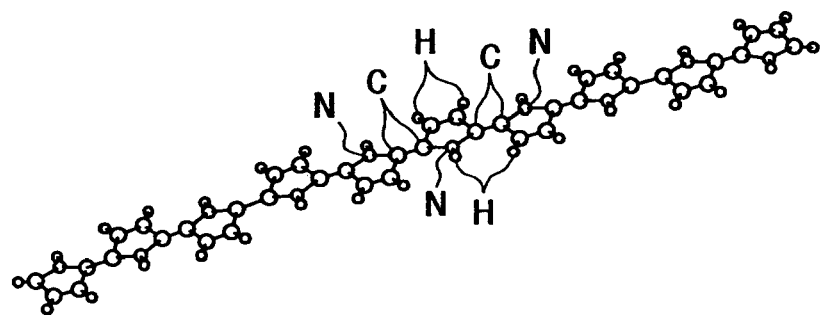
F I G. 6
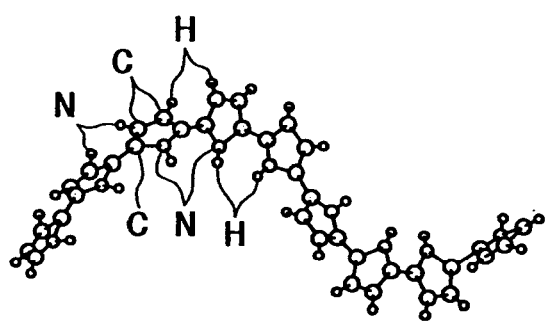
F I G. 7
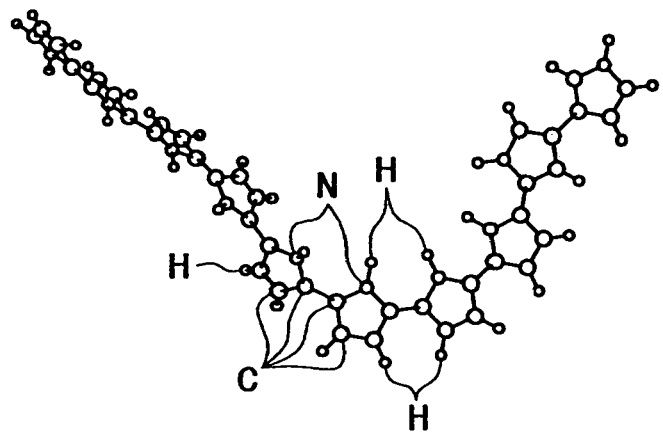

a: PROTON ADDITION AFTER
   −OH GROUP SUBSTITUTION
b: $Ag^+$ CONCENTRATION 0.04mol/l
c: $Ag^+$ CONCENTRATION 0.03mol/l
d: $Ag^+$ CONCENTRATION 0.02mol/l F I G. 1 2
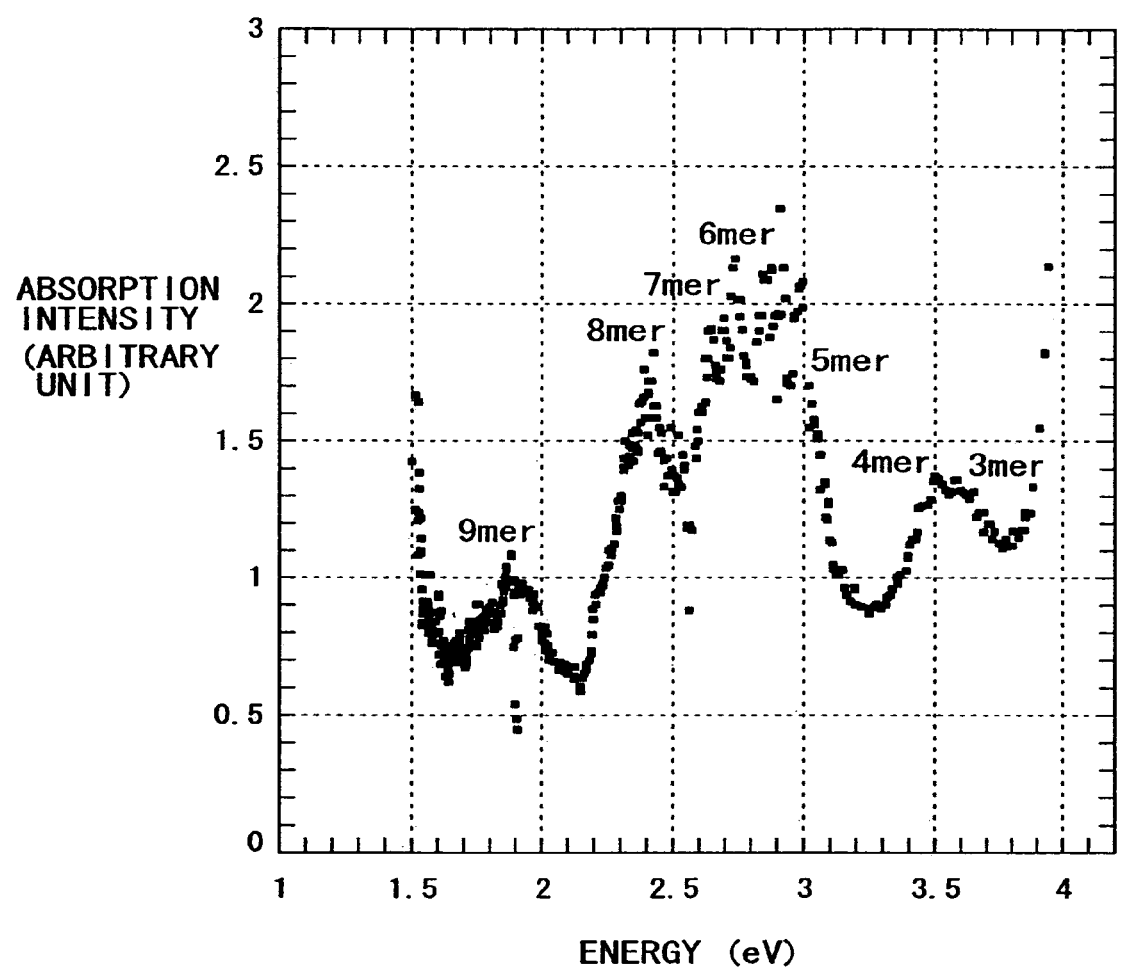

F I G. 1 9
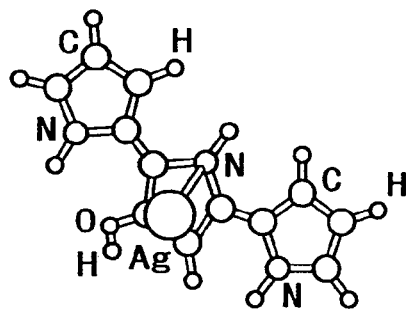
F I G. 2 0
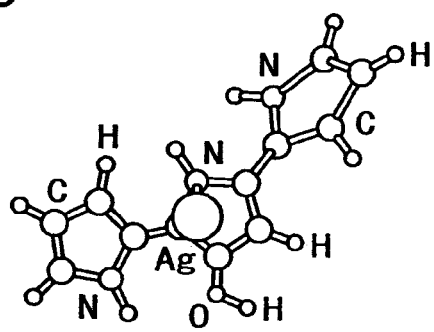
F I G. 2 1
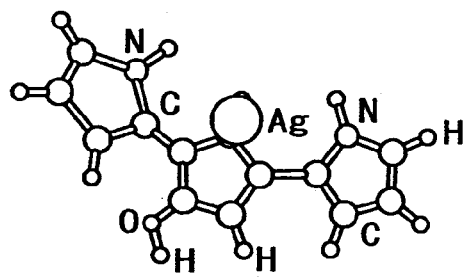
F I G. 2 2
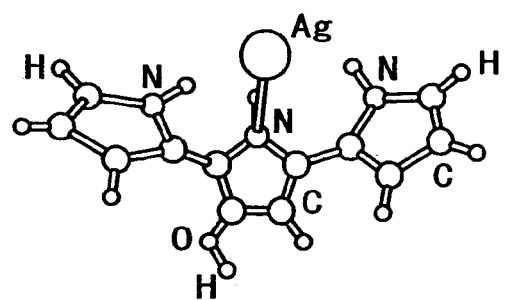

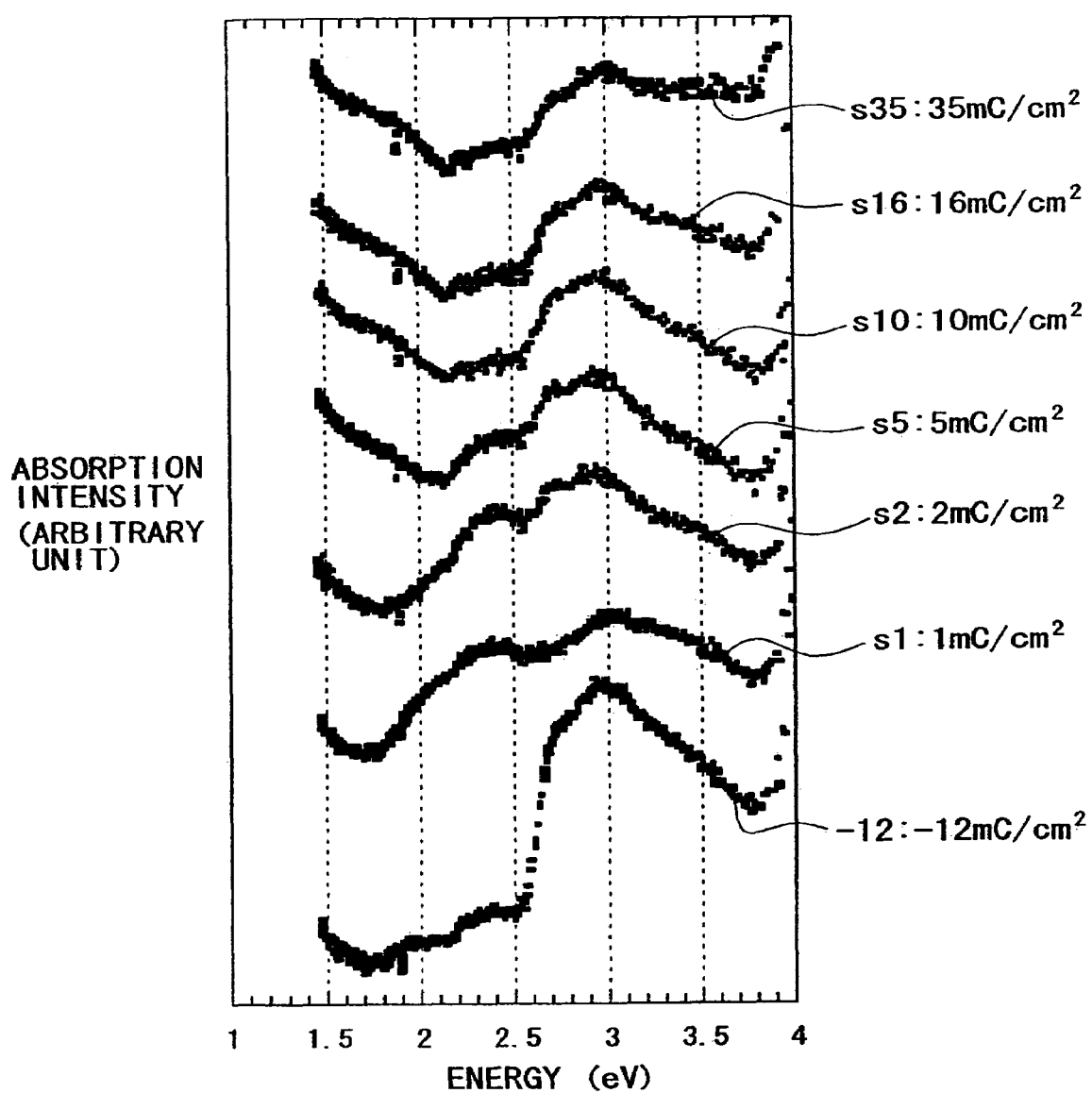

METAL COMPLEX OF HETEROCYCLIC AROMATIC COMPOUND

This is a continuation of application Ser. No. 10/468,982, filed Aug. 25, 2003, now U.S. Pat. No. 7,038,025 which is a 371 of international application PCT/JP02/13228, filed Dec. 18, 2002, which claims priority under 35 USC 119 to Japanese application 2001-396451, filed in Japan on Dec. 27, 2001, the entirety thereof being incorporated herein by reference.

TECHNICAL FIELD

The present invention relates to a metal complex of a heterocyclic aromatic compound.

BACKGROUND ART

In recent years, an increasing interest has been taken in molecular devices learnt from excellent structures and functions seen in organisms. Most of vital reactions pertain to physical and chemical processes through which proteins, such as enzymes, or functional coloring matter molecules pass at high efficiency and high selectivity. A lot of researches have been made in order to develop a new molecular device by artificially modeling after such a function.

However, as compared with the today's progress of the researches of organisms themselves such as genome decoding and elucidation of the functions of proteins, few novel molecular devices have appeared which are learnt from the functional principles in organisms. In practice, most of the researches are directed not toward the realization of a molecular device having a function learnt from an organism but toward the studies of a fabrication (orientation, arrangement, laminate film, or the like) which relates to a new device having the function not yet produced but with which the device can possibly be produced.

Accordingly, it is an object of the present invention to provide a novel metal complex of a heterocyclic aromatic compound which makes it possible to learn from the functional principles of enzymes in organisms and, particularly, to achieve favorable functions as molecular devices in technological fields.

DISCLOSURE OF INVENTION

The present invention pertains to a metal complex of a heterocyclic aromatic compound, comprising an acidic central atom comprised of a metal (for example, an acidic ion of a transition metal, such as Ag, as a central metal), and basic ligands comprised of a 5-membered heterocyclic aromatic compound, wherein the position of the central atom can be varied (particularly, the number of atoms (or the number of electrons) relating to the coordination ability can be regulated within the range of 1 to 5) by an internal factor such as transfer of an electric charge or an external factor such as application of an electric field.

According to the metal complex of a heterocyclic aromatic compound according to the present invention, the position of the central atom (namely, the number of atoms (or the number of electrons) relating to the coordination ability) can be regulated, and an original unstable structure can be automatically stabilized. This resembles the functional principle of an enzyme in an organism, causes a modulation of the structure of a derivative (inclusive of polymer) of the metal complex according to the change in the position of the central atom, thereby stabilizing the structure, and, particularly, can realize favorable functions as molecular devices in technological fields.

BRIEF DESCRIPTION OF DRAWINGS

FIG. 5 is a schematic diagram of a trans-isomer of a pyrrole oligomer in an embodiment of the present invention.

FIG. 6 is a schematic diagram of a cis (gauche)-isomer of a pyrrole oligomer in an embodiment of the present invention.

FIG. 7 is a schematic diagram of a cis-trans mixture of a pyrrole oligomer in an embodiment of the present invention.

FIG. 12 is a UV-visible absorption spectrum diagram of a solution of trimeric pyrrole cations, in an embodiment of the present invention.

FIG. 19 is a schematic diagram showing the case where silver is present on a β-site carbon atom on the side on which —OH group is present, in an embodiment of the present invention.

FIG. 20 is a schematic diagram showing the case where silver is present on an α-site carbon atom on the side on which —OH group is present, in an embodiment of the present invention.

FIG. 21 is a schematic diagram showing the case where silver is present on a nitrogen atom, in an embodiment of the present invention.

FIG. 22 is a schematic diagram showing an example in which silver is disengaged from a pyrrole ring, in an embodiment of the present invention.

FIG. 26 is a graph showing the variation in absorption spectrum when the charge state of a metal complex is varied, in an embodiment of the present invention.

BEST MODE FOR CARRYING OUT THE INVENTION

Now, the present invention will be described more specifically based on embodiments thereof.

In the metal complex of a heterocyclic aromatic compound based on the present invention, the 5-membered heterocyclic aromatic compound desirably contains an N (nitrogen) atom. In addition, the N atom is desirably protonated or having an sp3 hybrid orbital. Furthermore, a substituent group capable of intramolecular hydrogen bonding may be present on a β-site carbon atom of the heterocyclic aromatic compound.

Here, examples of the substituent group capable of intramolecular hydrogen bonding include —OH group, etc. Generally, a method of protonation for cutting away a double bond of carbon is easier to carry out, but the method is unfavorable because it hinders polymerization or a π-electron conjugated system. Therefore, in the present invention, a desirable method for putting the above-mentioned atom into the sp3 hybrid orbital is a method in which a substituent group capable of intramolecular hydrogen bonding, for example, an —OH group is introduced onto the β-site carbon atom of the heterocyclic aromatic compound, whereby predominance is given to coordination of metal ion to the nitrogen atom.

In addition, the transition metal ion is desirably acidic. Examples of the transition metal ion include the ions of atoms of Groups 1B to 5B of the periodic table; particularly, Ag is preferable, and Cu and Au may also be used. Furthermore, atoms such that the number of electrons in the d-orbital becomes 10 upon ionization may also be used, and examples of such atoms include Zn, Cd, Hg, etc.

The internal or external factor is indispensable for changing the position of the above-mentioned central atom so as thereby to obtain the above-mentioned effect. The internal factor is preferably transfer of an electric charge, whereas the external factor is preferably application of an electric field, a change in the acidicity of the surrounding environment, or the like. In this case, for example, the transfer of an electric charge is preferably |0 to 60| mC/cm² by a redox reaction, the application of an electric field is preferably application of a DC or AC voltage of |0.001 to 100| V between both electrode plates, and the acidity is preferably pH=0.01 to 14.

Pyrrole-Metal Complex

<Basic Structure of Metal Complex>

The metal complex of a heterocyclic aromatic compound according to the present invention is, specifically, desirably a metal complex of pyrrole or a metal complex of a derivative thereof.

Here, the derivative is a concept including compounds in which a functional group is introduced to the heterocyclic ring and also compounds in which pyrrole itself or other molecule, atomic group or the like is substituted for or added to a part of pyrrole.

<Pyrrole and Derivatives Thereof>

Next, the metal complex of a heterocyclic aromatic compound based on the present invention will be described more in detail.

Figure 1:
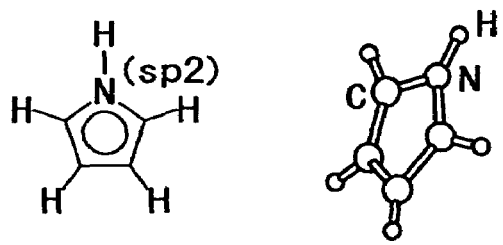
FIG. 1 is a schematic diagram of a pyrrole molecule in an embodiment of the present invention.

The following structural formula (1) and FIG. 1 show a pyrrole molecule, which is a 5-membered heterocyclic aromatic compound containing one nitrogen atom.

Structural formula (1):

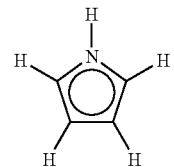

The pyrrole molecule has a structure in which the lone pair of the nitrogen atom is non-localized on the aromatic ring, so that it shows little basicity ($pK_b$ 0 to $2.5 \times 10^{-14}$). Incidentally, the derivatives of pyrrole in many cases constitute a basic matter of an organism, as in the cases of hemoglobin, chlorophyll and alkaloid. In addition, as is clear from the structural formula (1) and FIG. 1, pyrrole has a π-electron conjugated system containing two electrons of the nitrogen atom, and is easily polymerized to be an oligopyrrole or polypyrrole.

Figure 2:
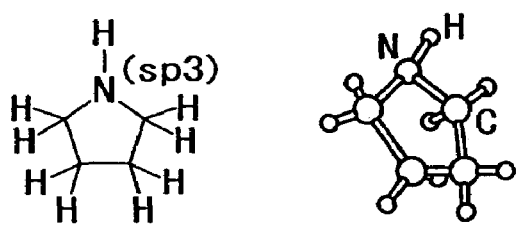
FIG. 2 is a schematic diagram of a pyrrolidine molecule in an embodiment of the present invention.

The following structural formula (2) and FIG. 2 show a pyrrolidine molecule.

Structural formula (2):

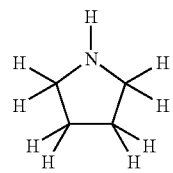

The pyrrolidine molecule shows a strong basicity ($pK_b \sim 10^{-3}$), and can be produced by reducing the pyrrole molecule. The pyrrolidine molecule shows the properties of a chain secondary amine because electrons of the nitrogen atom take an sp3 hybrid orbital, and can form a salt which will easily be crystallized, but it cannot be polymerized because it has no double bond.

As above-mentioned, the pyrrole molecule intrinsically has such a property that the π-electron conjugated system is varied variously upon some changes in structure as shown in the structural formulas (1) and (2) and FIGS. 1 and 2, and can easily be polymerized. Besides, it is known that in an oxidized state of a polymeric film of the pyrrole molecule, a band is formed due to the polaron movement of the conjugated system, resulting in the presence of conductivity. Hitherto, however, attention has been paid only to the properties of the pyrrole polymer as the conductive polymer, and a research of the pyrrole polymer as a remarkable functional device has not been conducted (Even in dealing with the pyrrole polymer as an electrochromic device, only the high degree of conductivity is utilized.).

Other 5-membered heterocyclic aromatic compounds than pyrrole include thiophene which contains a sulfur atom in place of the nitrogen atom and furan which contains an oxygen atom in place of the nitrogen atom. These have an electron affinity energy and an ionization potential which are substantially equal to each other, so that they can develop conductivity due to both cation doping and anion doping. Therefore, thiophene and furan can be used as each of both electrodes, and they have been studied principally in relation to battery. However, the pyrrole molecule has an electron affinity energy of 0.3 eV, which is extremely small as compared with its ionization potential of 3.8 eV, so that it cannot be subjected to cation doping. Therefore, the pyrrole molecule has not been regarded as much important, even in the research fields relating to battery.

Pyrrole Oligomer

Figure 3:
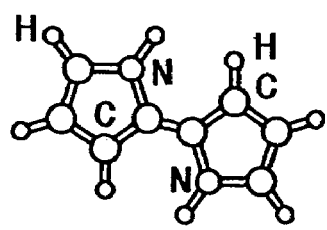
FIG. 3 is a schematic diagram of a pyrrole-pyrrole molecule in a trans-isomer having nitrogen atoms in symmetric positions in an embodiment of the present invention.
Figure 4:
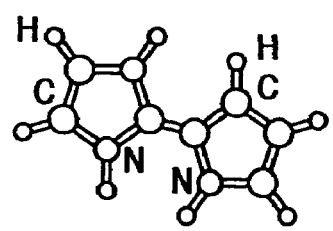
FIG. 4 is a schematic diagram of a pyrrole-pyrrole molecule in a cis-form having nitrogen atoms on the opposite sides in an embodiment of the present invention.

A pyrrole oligomer formed by polymerization of the pyrrole molecule tends to take the π-bond in the molecule plane in order to enhance the conjugated system. Therefore, for example, a pyrrole-pyrrole molecule (dimmer) as a pyrrole oligomer is stable when it takes the form of a trans-isomer having the nitrogen atoms at symmetric positions as shown in FIG. 3 and when it takes the form of a cis-isomer having the nitrogen atoms on the opposite sides as shown in FIG. 4. Here, in comparison of the trans-isomer and the cis-isomer with each other, it has been reported that the trans-isomer has a lower energy and is stabler in the case where one molecule is present in vacuum, but the cis-isomer is formed more easily depending on the surrounding solvent molecules, electrolyte or the like ("First evidence of crystalline structure in conducting polythiophene", F. Garnier, et al., J. Mater. Science, 20 (1985) 2687-2694.).

Here, where the dihedral angle in the trans-isomer is 0° and the dihedral angle in the cis-isomer is 180°, a structure with a dihedral angle of 90° is high on an energy basis and is therefore instable. Namely, when it is intended to achieve a conformation change from the trans-isomer to the cis-isomer, it is necessary to go over the high energy mount of the instable structure.

As to the dihedral angle, the same properties are shown even when an oligomer with an increased number of pyrrole molecules is formed. It should be noted here that, as shown in FIGS. 5 to 7, in the cases of for example the octamer and higher oligomers, the cis-isomer with a dihedral angle of 180° suffers a steric hindrance, so that a structure with a dihedral angle of about 140 to 160° is stable, and a spiral structure is formed; besides, a mixture of trans-isomer and cis-isomer may also be formed in some cases.

The present inventors, paying attention to substances such as the pyrrole molecule which have basicity and the specificity of a conjugated system, have made intensive and extensive studies for synthesizing a functional molecule based on a novel principle (for example, those with the dihedral angle varied variously), and, as a result of their studies, have found out the metal complex of a heterocyclic aromatic compound based on the present invention.

The metal complex of a heterocyclic aromatic compound based on the present invention is, for example, the above-mentioned pyrrole-metal complex (in which $0<n\leq 5$, i.e., the number n of atoms relating to the coordination ability is an integer of 1 to 5, which can be defined as that the number of electrons relating to the coordination ability is in the range of 1 to 6) or the like in which the above-mentioned basic ligands comprised of the 5-membered heterocyclic aromatic compound are in coordination to the silver ion as the transition metal ion and in which, preferably, an —OH group as the substituent group capable of intramolecular hydrogen bonding is bonded to the β-site carbon atom of the heterocyclic aromatic compound.

Mechanism of Pyrrole Complexing

<Complexing Reaction>

In the complexing, for example, the pyrrole molecule represented by the above structural formula (1) is used as the starting material, the nitrogen atom is protonated by controlling the proton concentration to change the basicity, thereby forming a pyrrole derivative, and the pyrrole derivatives are put into coordination to the transition metal ion, for example, the silver ion to form the complex. For example, 1 mol of silver ions can be bonded to 2.5 mol of pyrrole molecules. It should be nodded here that, depending on the degree of protonation, the nitrogen atom is in the sp3 state and the basicity is so strong that the silver ion is put into coordination bond to that portion, resulting in the formation of a complex in which the sp3 state is stabilized.

In this case, since the complex with strong basicity forms a complex with strong polarization, the position change of the silver ion (namely, the regulation of the number of atoms (or the number of electrons) relating to the coordination ability) due to the above-mentioned internal or external factor cannot be achieved, and, since the double bond is lost, polymerization cannot be achieved. Therefore, in the protonation, complete protonation is not conducted. That is, it is desirable that the reaction is not brought to such a stage as to form the pyrrolidine molecule represented by the above structural formula (2). Incidentally, it is generally easier to effect the protonation by breaking up the double bond, but it is unfavorable because it produces a bad effect on the polymerization or the π-electron conjugated system. Therefore, as the method for protonation of the nitrogen atom, the above-mentioned substituent group capable of intramolecular hydrogen bonding, for example, the —OH group is substituted onto the β-site carbon atom of the heterocyclic aromatic compound, whereby the sp3 property of the nitrogen atom is enhanced.

Namely, it is a characteristic feature that the transition metal ion, for example, the silver ion is put into coordination to the pyrrole derivatives, and the position of the silver ion is changed in the molecule by the above-mentioned internal or external factor, and then the steric structure can be changed.

<Effect of Internal or External Factor>

Attention should be paid to the fact that the metal complex of a heterocyclic aromatic compound based on the present invention has such a property that the number of atoms (or the number of electrons) relating to the coordination ability can be regulated by the above-mentioned internal or external factor.

Namely, for example, the conformation can be changed by externally modulating the electron state of the pyrrole oligomer. Specifically, although the possible values of the dihedral angle are stable only in the two forms of the trans-isomer and the cis-isomer (thermal fluctuations of about ±10° are present, though), a high energy state such as that with a dihedral angle of about 90° can also be stabilized by the interaction between the acidic transition metal ion ($Ag^+$), which is the modulation factor, and the pyrrole oligomer.

Figure 8:
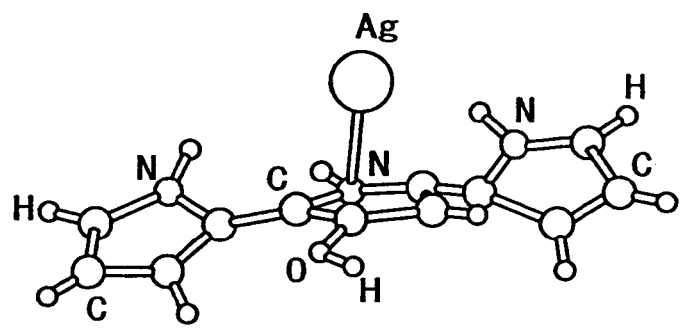
FIG. 8 is a schematic diagram of an example in which the structure is stabilized by a regulating factor notwithstanding the dihedral angle is near 135°, in an embodiment of the present invention.

FIG. 8 is a schematic diagram showing one example in which a structure is stabilized by the modulation factor ($Ag^+$) even though the structure has a dihedral angle of about 135°.

Method of Producing Pyrrole Oligomer

<Production of Pyrrole-Metal Complex>

Next, one example of the method of producing a pyrrole-metal complex as the metal complex of a heterocyclic aromatic compound based on the present invention will be described.

Pyrrole monomer is mixed with a propylene carbonate solution so that its concentration is 0.1 mol/l. For the purpose of substitution of a hydroxyl group onto the β-site of the pyrrole molecule, 1% by weight of water is added to the mixed solution. Since the dissolved oxygen plays an important role, the solution is not subjected to bubbling with nitrogen gas, bubbling with argon gas or the like.

Then, for protonation of the nitrogen atom in the pyrrole molecule, an acid is gradually added to the solution so as to gradually raise the proton concentration. The acid may be $HClO_4$ or $HCF_3SO_3$, which is dissociated as a strong acid in the propylene carbonate solution. Here, the protonation of the nitrogen atom owing to the proton concentration can be easily monitored through infrared absorption spectrum. For example, in order to provide such a basicity as to form a complex, it suffices to pay attention to the spectrum near 2300 $cm^{-1}$, which is the N—H stretching vibration band of the secondary amine salt.

<Production of Pyrrole Oligomer>

Subsequently, polymerization of the pyrrole ring for complexing with the transition metal and a pyrrole ring lower in basicity than the just-mentioned pyrrole ring and an ordinary pyrrole ring is conducted.

The ionization potential of the pyrrole molecule having basicity is inversely proportional to the basicity; as the basicity is higher, the ionization potential is lower and the polymerization energy is lower, so that the polymerization takes place more easily. When the polymerization is conducted taking this into account, the pyrrole oligomer having a desired structure can be produced.

For example, silver ion is used as an oxidizing agent for use in polymerization (oligomerization) of pyrrole and as the above-mentioned transition metal ion. When the basicity of the pyrrole ring is preliminarily adapted to the acidity of the silver ion, a complex can be easily formed. (For example, the silver ion is preliminarily subjected to aqueous salvation, and the water ligands are subjected to ligand exchange with pyrrole rings. Since water is a hard base, it is easily replaced by a soft base when brought into contact with the soft base.) The silver ion suitable for the oxidative polymerization and the complex formation can be determined by the concentration ratios among the silver ion, the water molecule and the pyrrole monomer.

<Confirmation of Pyrrole Oligomer>

Figure 9:
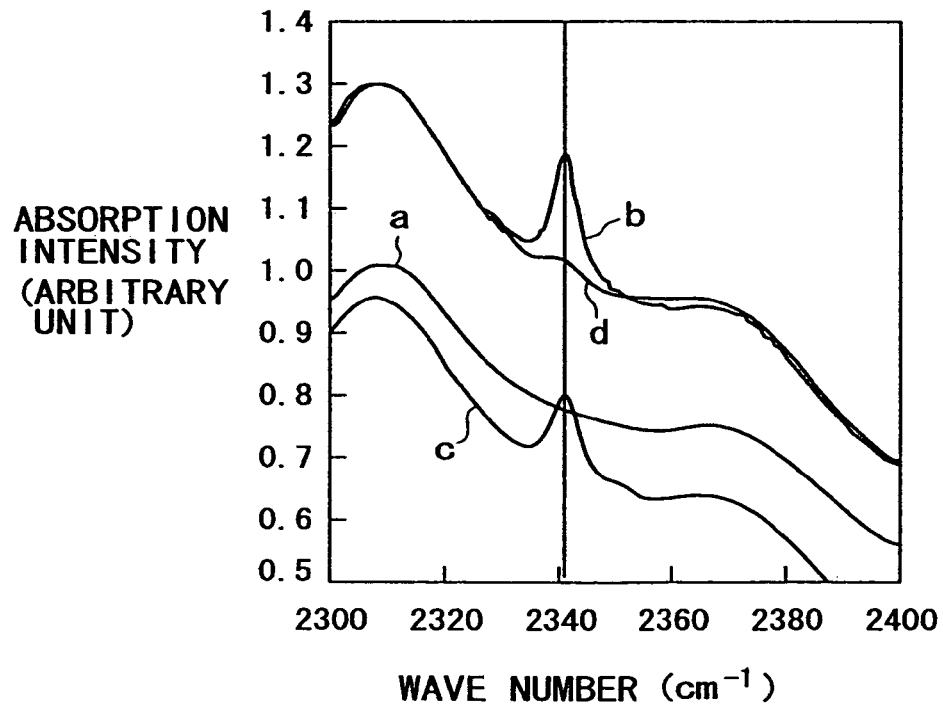
FIG. 9 is an absorption spectrum diagram of a complexed pyrrole molecule in an embodiment of the present invention.

The formation of the pyrrole complex with silver can be confirmed by a steep peak shape near 2300 $cm^{-1}$ of the amine salt and the absorption intensity thereof, as shown in FIG. 9. In FIG. 9, the peak intensity varies with the Ag concentration, as indicated by symbols a to d.

Figure 10:
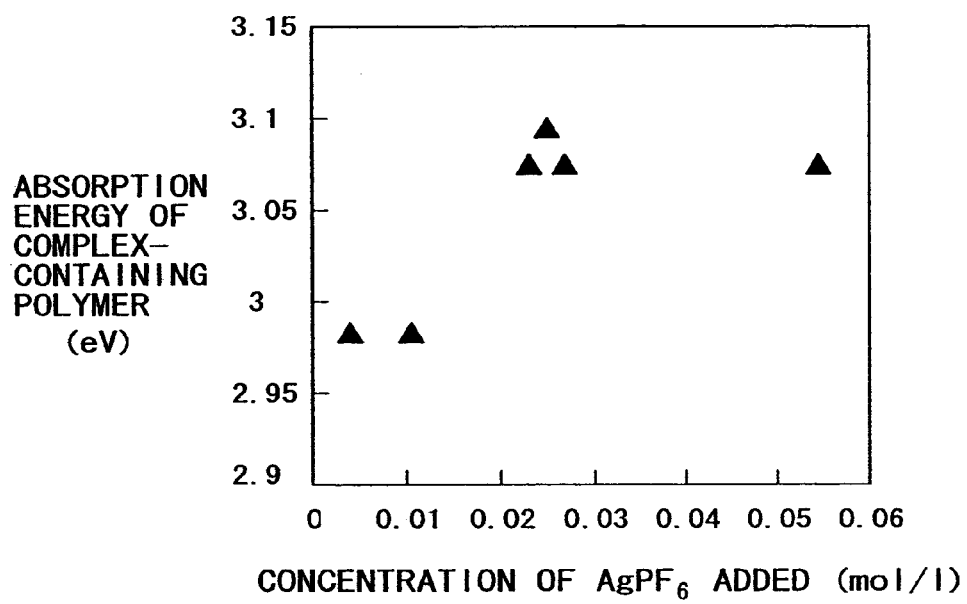
FIG. 10 is a graph showing the concentration of silver ion necessary for forming a complex, in an embodiment of the present invention.

FIG. 10 is a graph showing one example of silver ion concentration necessary for the complex formation. It is seen that when the pyrrole concentration is 0.1 mol/l and $AgPF_6$ is used, it is preferable to set the concentration of $AgPF_6$ to be not less than 0.02 mol/l.

Figure 11:
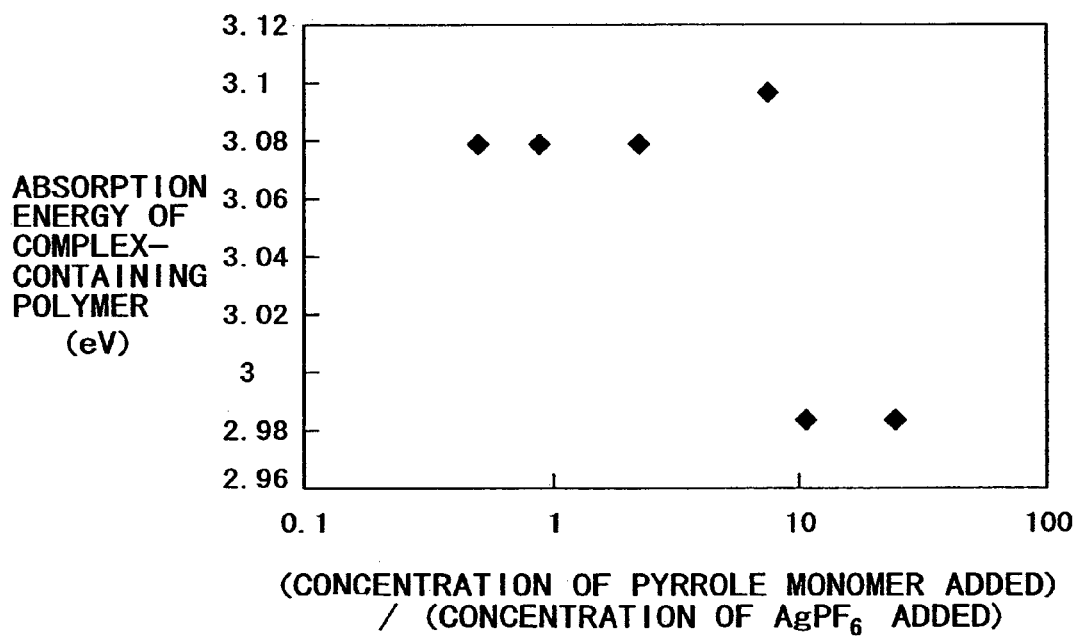
FIG. 11 is a graph showing the concentration ratio of silver ion and pyrrole monomer necessary for oxidative polymerization, in an embodiment of the present invention.

FIG. 11 is a graph showing the concentration ratio between silver ion and pyrrole monomer necessary for the oxidative polymerization. It is seen that it is preferable to set the concentration ratio to be not more than 10.

In addition, the number of the pyrrole rings polymerized can be checked through visible absorption spectrum, and the number can be easily confirmed by the difference in π–π* transition energy band gap. The number of the pyrrole rings to be polymerized can be controlled by appropriately varying the kind and concentration of the electrolyte, reaction time, and, further, the density and viscosity of the solvent. Naturally, the number may be controlled chemically. (Reference: S. Martina, V. Enkelmann, A-D. Schluter and G. Wegner, Synth. Met., 51, 299 (1992))

FIG. 12 is a graph showing a UV-visible absorption spectrum of a mixed solution of a pyrrole oligomer in the form of a trimeric cation ($AgPF_6$: 0.04 mol/l; pyrrole: 0.10 mol/l; reaction time: 72 hr).

Figure 13:
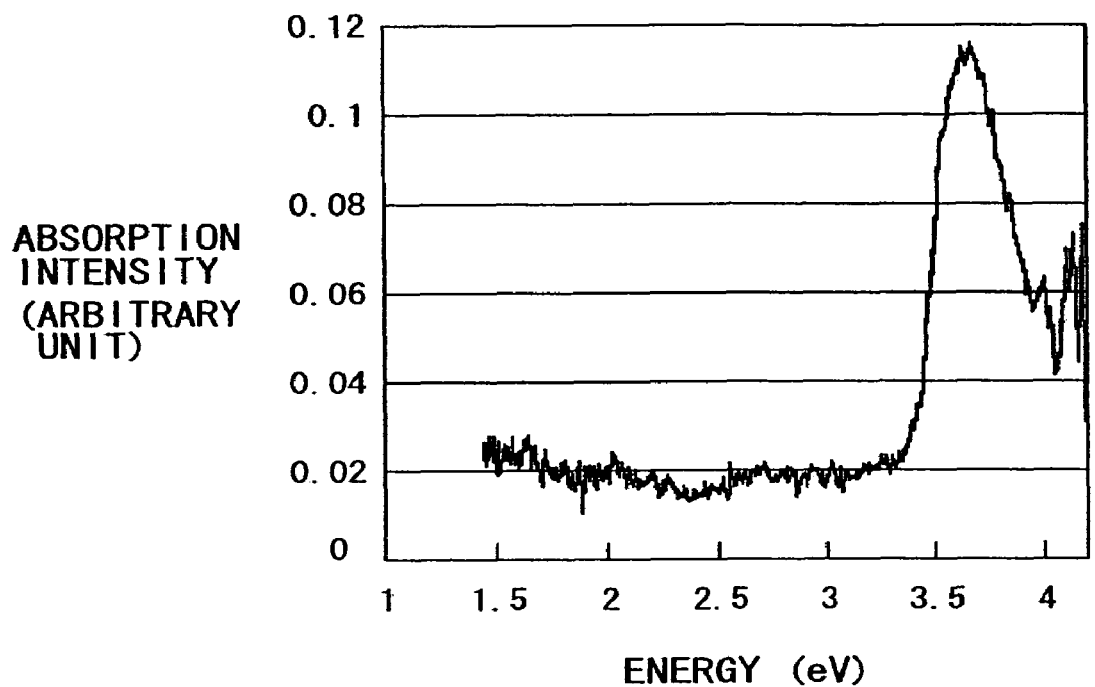
FIG. 13 is a UV-visible absorption spectrum of a pyrrole oligomer solution containing only the trimer, in an embodiment of the present invention.

In addition, FIG. 13 is a graph showing a UV-visible absorption spectrum of a pyrrole oligomer solution containing only the trimer ($AgBF_4$: 0.10 mol/l; pyrrole: 0.1 mol/l; reaction time: 192 min).

Figure 14:
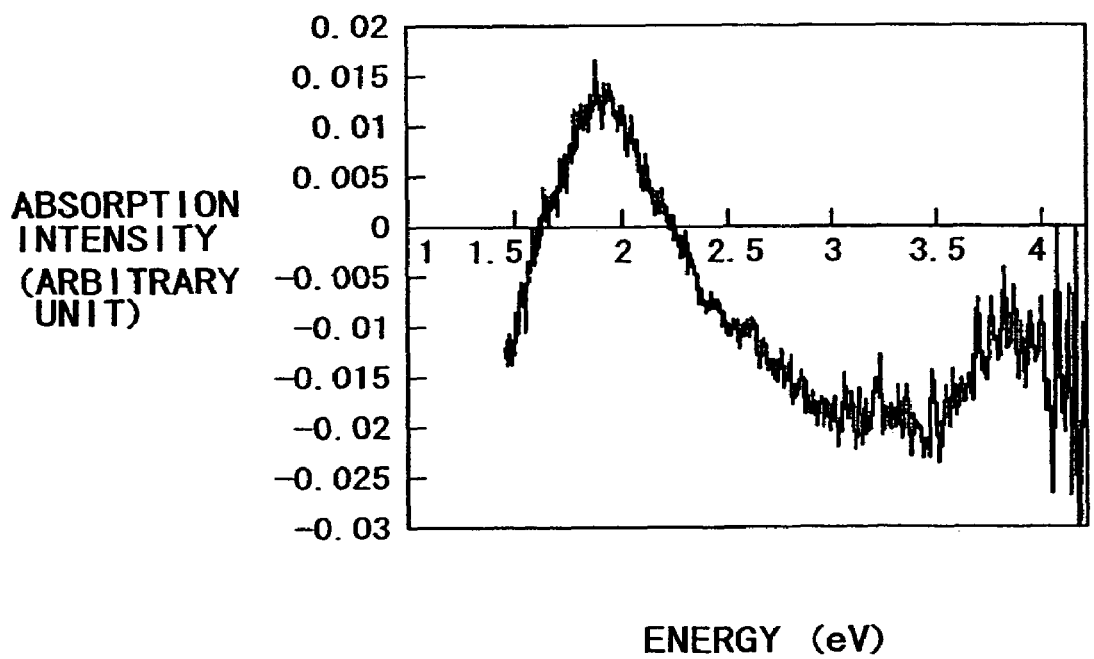
FIG. 14 is a UV-visible absorption spectrum diagram of a pyrrole oligomer solution containing only the nonamer, in an embodiment of the present invention.

Further, FIG. 14 is a graph showing a UV-visible absorption spectrum of a pyrrole oligomer solution containing only the nonameric cation ($AgNO_3$: 0.04 mol/l; pyrrole: 0.1 mol/l; reaction time: 100 hr).

Conformation Modulation of Pyrrole Oligomer

<Influence of Internal or External Factor>

Next, the activities of silver ion when conformation modulation due to the above-mentioned internal or external factor is caused while using the metal complex of a heterocyclic aromatic compound based on the present invention, for example, a pyrrole oligomer were observed through infrared absorption spectrum. FIGS. 15 to 18 show the variations in absorption intensity when, for convenience, electric charges are gradually added starting from an oxidized state, although the reaction is reversible.

Figure 15:
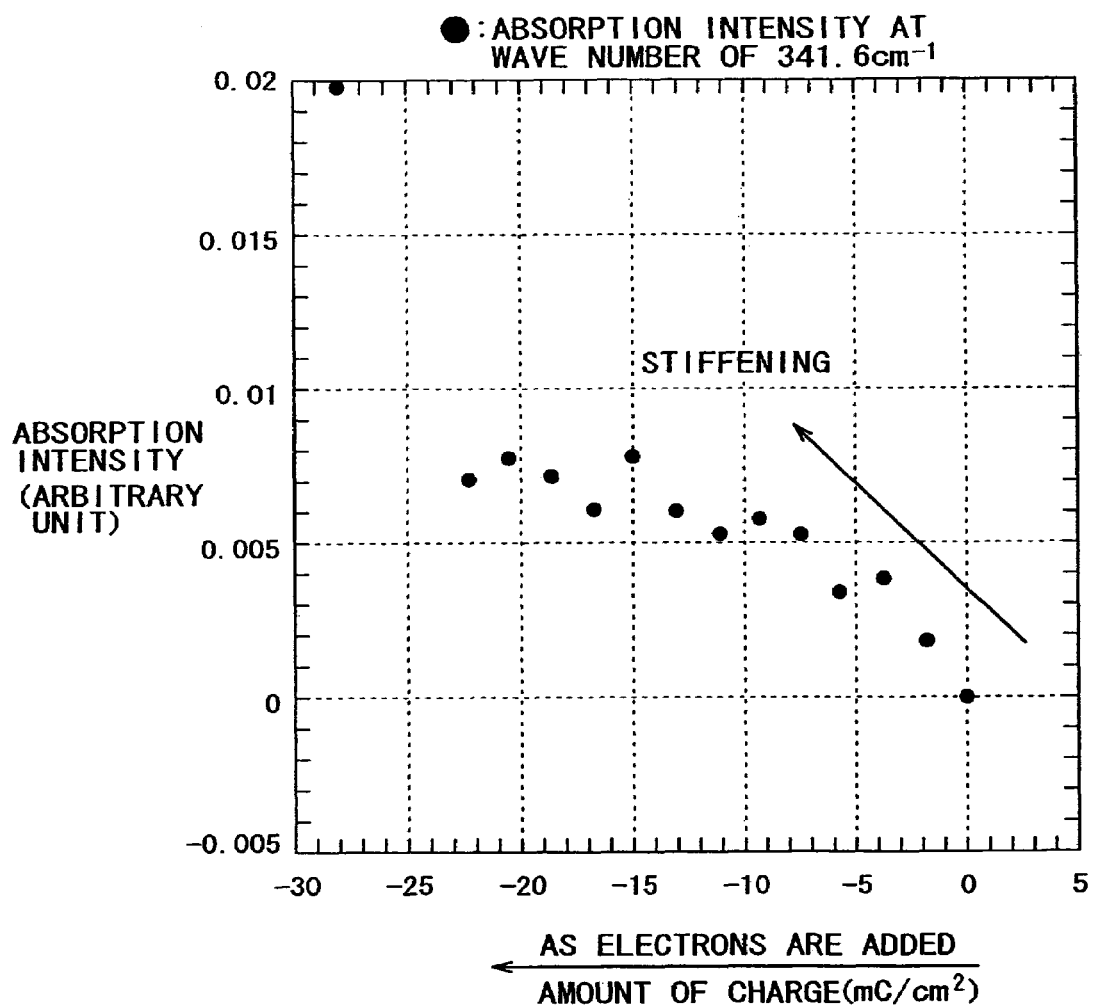
FIG. 15 is an absorption spectrum diagram of an N—H structure portion (str.) of a secondary amine salt, in an embodiment of the present invention.

FIG. 15 is a graph showing the variations in absorption intensity of an N—H structure portion (str.) of a secondary amine salt complexed with silver. As is clear from FIG. 15, as the amount of electrons added is increased, the N—H structure portion of the complexed pyrrole ring undergoes steric hindrance, and flexibility is gradually lost. However, relaxation does not take place.

Figure 16:
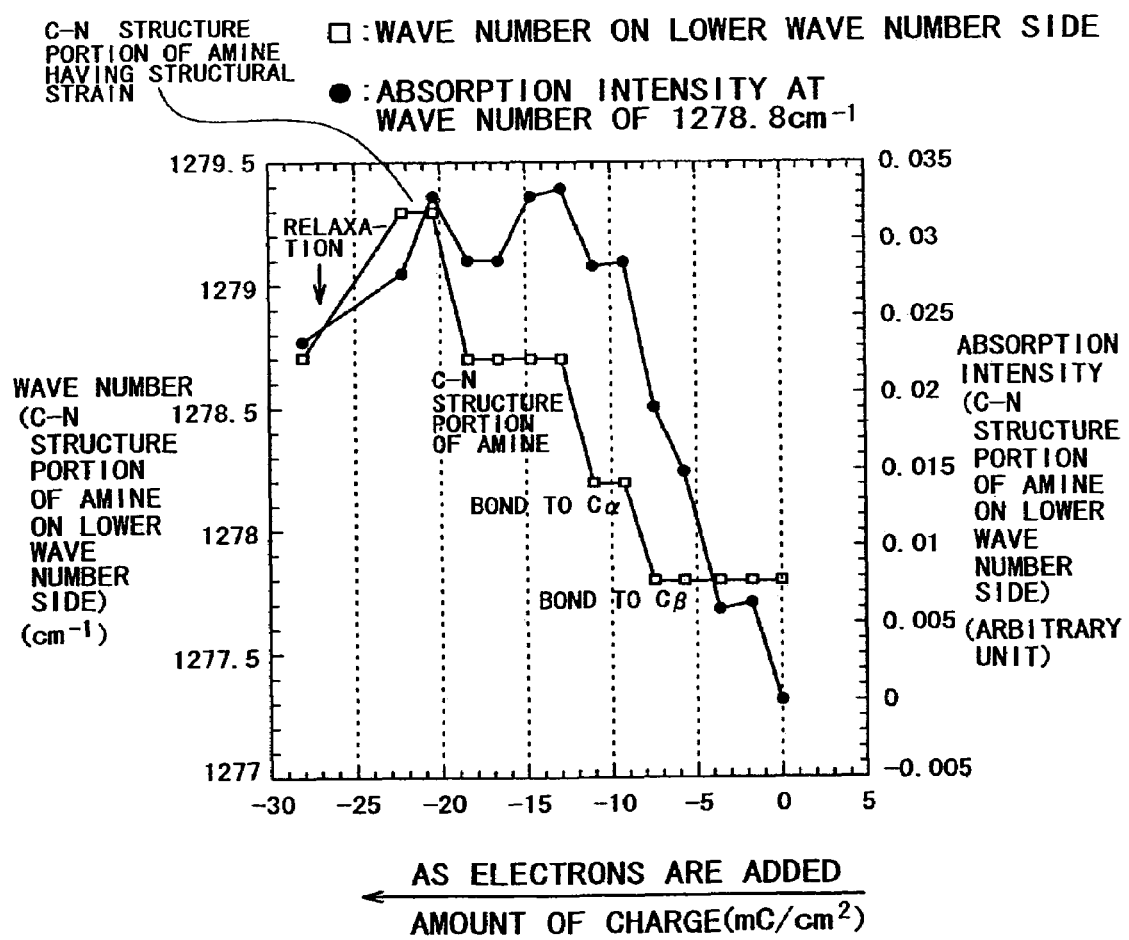
FIG. 16 is a graph showing variations in wave number and absorption intensity due to charge amount at a C—N structure portion (str.) on the side on which —OH group of a secondary amine salt is present, in an embodiment of the present invention.

In addition, FIG. 16 is a graph showing the variations in absorption intensity of a C—N structure portion of a secondary amine salt complexed with silver on the side on which the —OH group is present.

Figure 17:
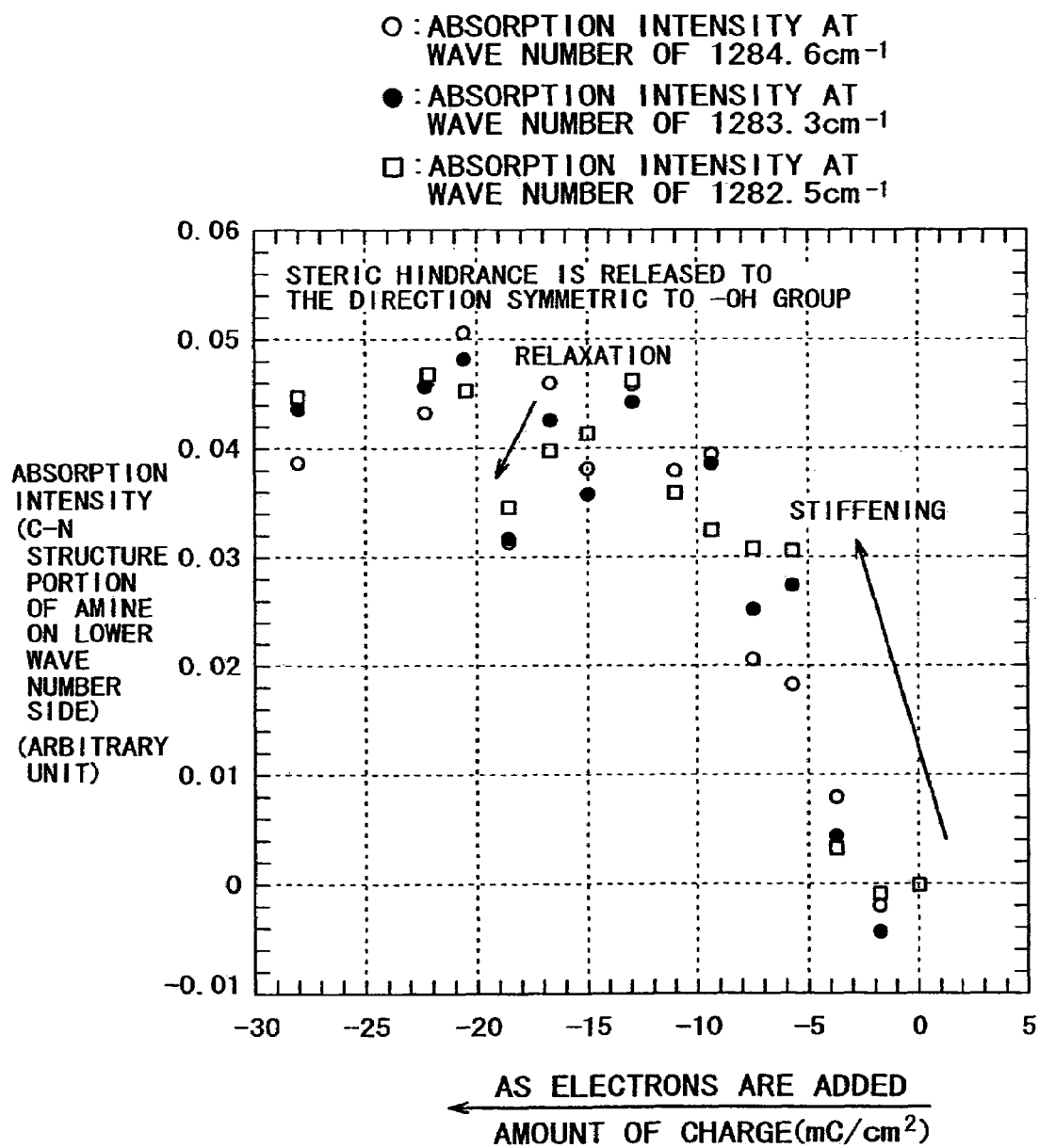
FIG. 17 is an absorption spectrum diagram of a C—N structure portion (str.) on the side on which —OH group of a secondary amine salt is absent, in an embodiment of the present invention.

Further, FIG. 17 is a graph showing the variations in absorption intensity of a C—N structure portion of a secondary amine salt complexed with silver on the side on which the —OH group is absent. As is clear from FIG. 17, as the amount of electrons added is increased, a steric hindrance is caused, although there is no bond to the C atoms on the side on which the —OH group is absent.

Figure 18:
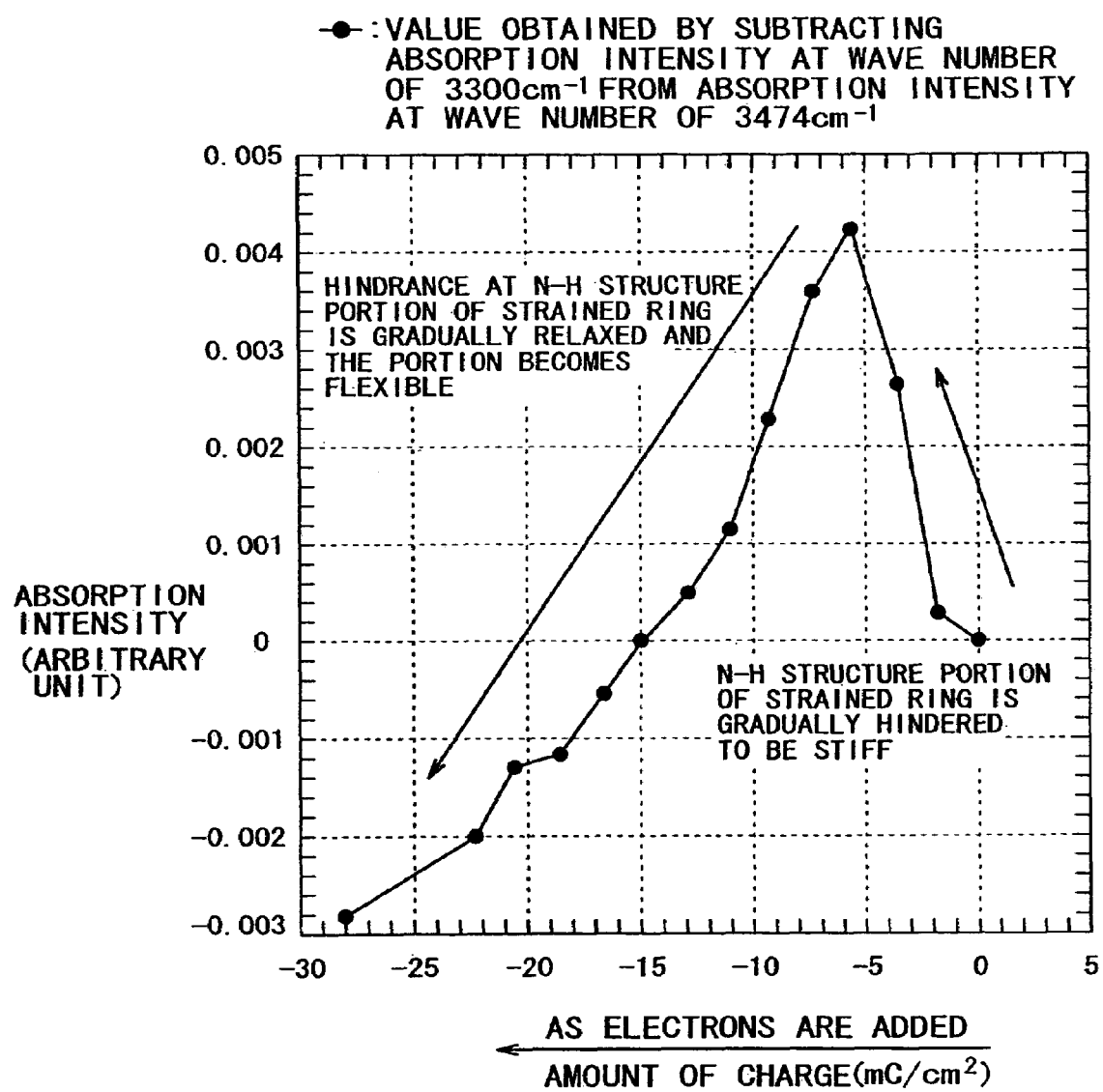
FIG. 18 is a graph showing variations in absorption intensity of an N—H structure portion (str.)of the pyrrole ring which has a structural strain and in which the nitrogen atom is protonated, in an embodiment of the present invention.

Besides, FIG. 18 is a graph showing the variations in absorption intensity of an N—H structure portion of a pyrrole ring having a structural strain.

As is clear from FIGS. 15 to 18, an increase in absorption intensity indicates an increase in the concentration of the matter in consideration itself or an increase in asymmetry. The shift of a vibration absorption band in an infrared absorption spectrum to the side of higher wave number (the shift to the side of higher energy) indicates that the intrinsic vibration constant itself is increased (improvement of conjugated system and strain of structure), irrespective of hindrance or relaxation, and/or that the weights of both ends of a functional group are reduced.

<Discussion of Structural Change and Evaluation of Physical Properties>

Based on the results obtained from the movements of the molecular state generating the absorption intensity variation and the wave number shift as above, a computation for structural optimization was conducted, the results being shown below. It is remarked that the experimental results are a fact, but they are computational results and rather one of interpretations, so that the results are not yet fully established.

The silver ion is initially present on the β-site carbon atom on the side where the —OH group is present, as shown in FIG. 19. The nitrogen atoms of the pyrrole molecules disposed on both sides of the complexed pyrrole molecule as the metal complex of a heterocyclic aromatic compound based on the present invention move to the positions nearest to the silver ion in order to bond to the silver ion. In this instance, the dihedral angle formed by the complexed pyrrole molecule and the pyrrole molecules on both sides thereof is close to that in the state of the trans-isomer.

When electric charges are added to the state of FIG. 19, the silver ion moves onto the α-site carbon atom on the side on which the —OH group is present, and the dihedral angle formed with the pyrrole molecules on both sides takes such a value that the nitrogen atom is disposed nearest to silver, as shown in FIG. 20. Although the dihedral angle formed by the complexed pyrrole molecule and the pyrrole molecules on both sides thereof is in the state of the trans-isomer, the side on which the —OH group is absent is not affected by the unpaired electron of oxygen, so that the trimer is stabilized at an angle of 90°.

When an electric charge is further added, the silver ion moves onto the nitrogen atom as shown in FIG. 21, and, thereafter, it slips out to the side opposite to the side on which the —OH group is present. The dihedral angle formed by the complexed pyrrole molecule and the pyrrole molecules on both sides thereof is close to that in the state of the cis-isomer.

The dihedral angle formed by the complexed pyrrole molecule and the pyrrole molecules on both sides thereof always takes such a value that the nitrogen atom is disposed nearest to the silver ion. Then, the dihedral angle formed by the complexed pyrrole molecule and the pyrrole molecules on both sides thereof is now free of influence of the oxygen atom on both sides, so that the trimer is twisted symmetrically and is stabilized at an angle of about 45°.

Figure 23:
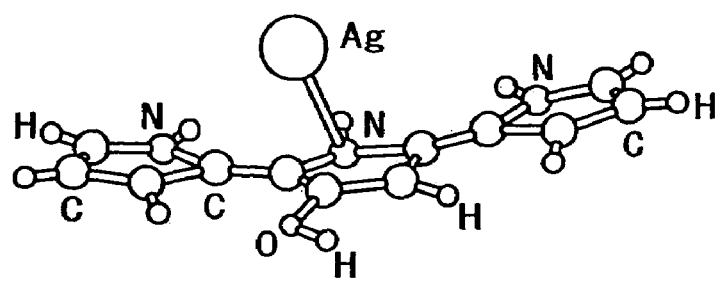
FIG. 23 is a schematic diagram of another example in which silver is disengaged from the pyrrole ring, in an embodiment of the present invention.

In addition, as shown in FIGS. 22 and 23, when the silver ion is completely set aside from the complexed pyrrole molecule, all of the three pyrrole molecules bonded to each other tend to take a conjugated system in a plane at equal distance from the silver ion, and is stabilized in that state.

From the foregoing, it has been shown that the conformation may be modulated from the trans-isomer to the cis-isomer by the control of the electric charge, and the bonding conditions may be varied so that the instability of the structure is stabilized by the silver ion. Specifically, the number n of atoms relating to the coordination ability of pyrrole can be varied in the range of $0 < n \leq 5$.

Accordingly, the metal complex of a heterocyclic aromatic compound based on the present invention is characterized in that it has a multiplicity of kinds of stable positions, instead of one kind of stable position.

In addition, the metal complex of a heterocyclic aromatic compound based on the present invention can show variations in color of visible absorption spectrum even after formation of a film, since the conjugated system therein can be modulated.

Figure 24:
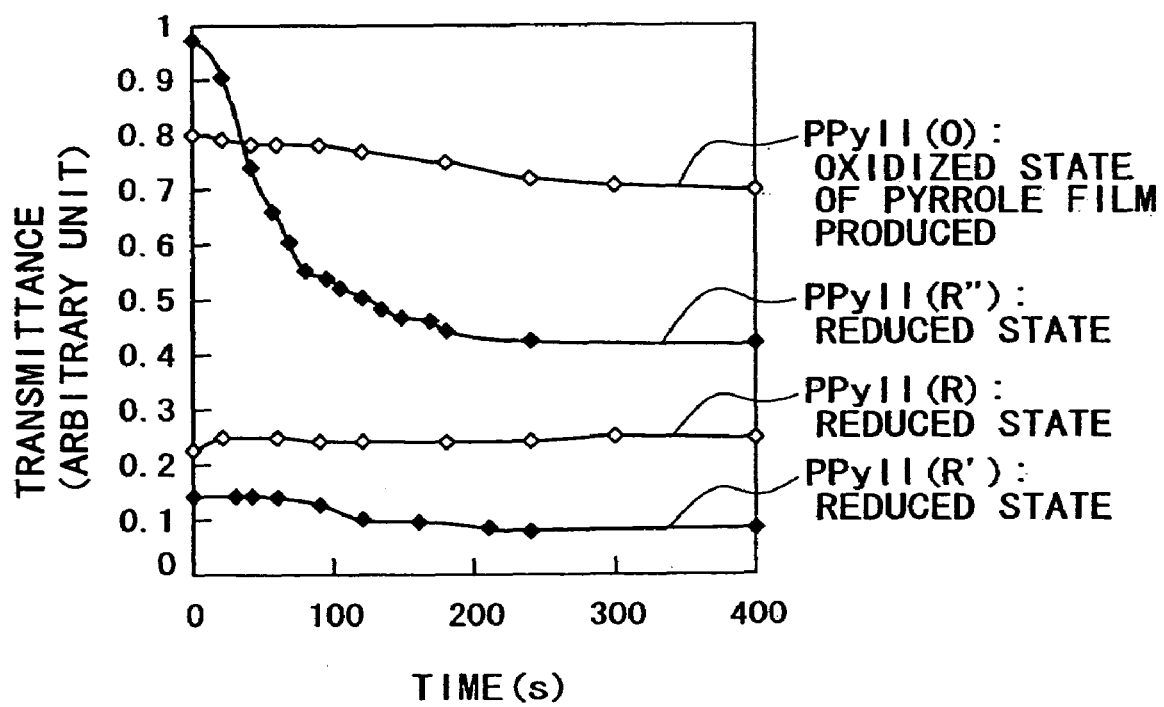
FIG. 24 is a graph showing the relationship between the variation in transmittance for white light and memory time, of a metal complex of pyrrole based on the present invention, in an embodiment of the present invention.

FIG. 24 is a graph showing the relationship between variation in transmittance for white light of a film of the metal complex of a heterocyclic aromatic compound and memory time. It is seen from the figure that various transmittances can be obtained depending on the conformation of the pyrrole rings, and that a memory function is present.

Figure 25:
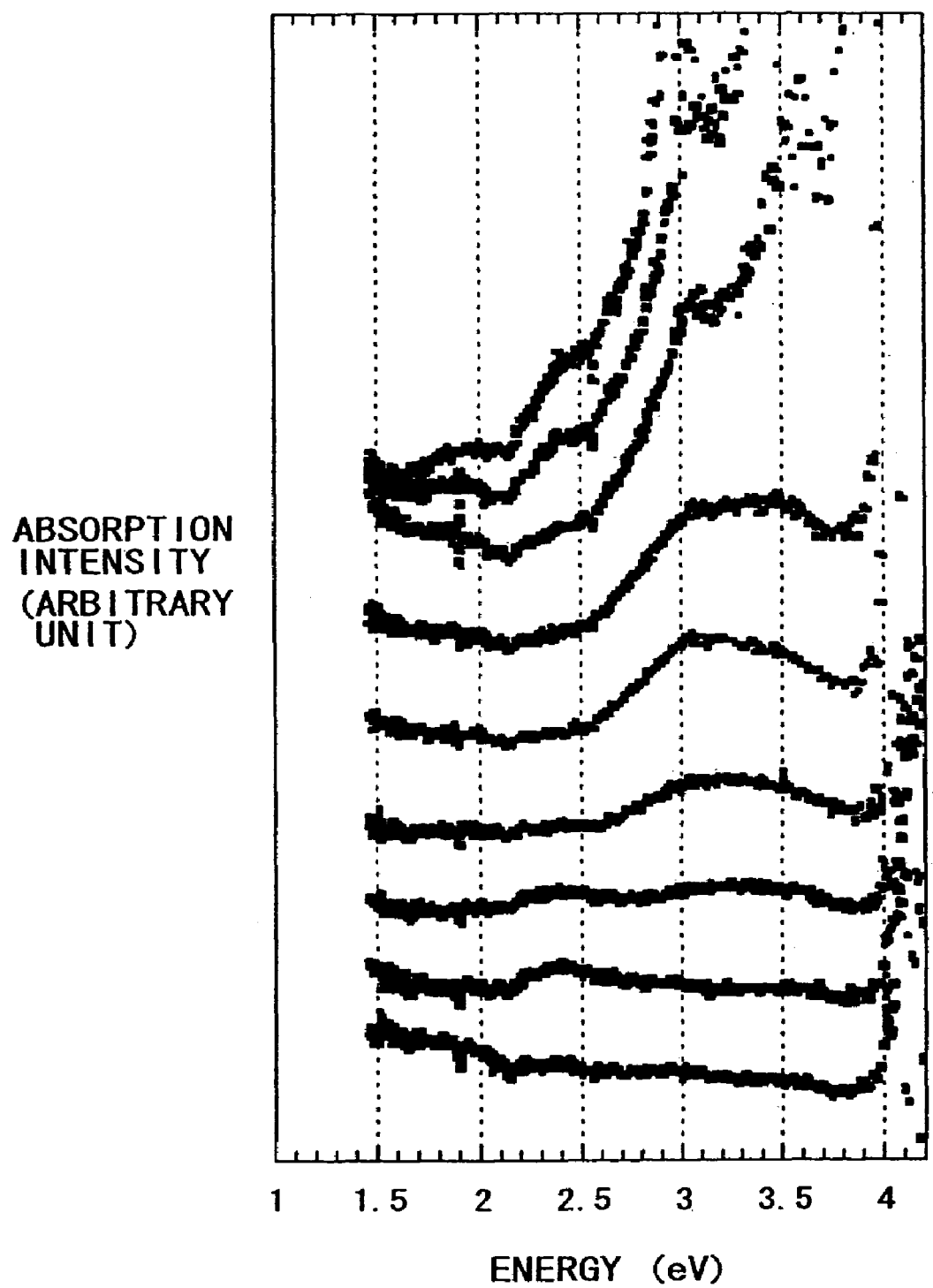
FIG. 25 is a graph showing the variation in absorption spectrum when the charge state of a metal complex is varied, in an embodiment of the present invention.

Besides, FIGS. 25 and 26 are graphs showing the variations in absorption spectrum when the charge state is varied. Incidentally, the axis of abscissas corresponds to the energy of UV and visible rays; for example, 2 eV means light with a wavelength of 620 nm, and 4 eV means light with a wavelength of 310 nm.

Here, the control of electric charge amount (the transfer of electric charge) may be mentioned as the internal factor, and the equivalent phenomenon can be observed upon application of an electric field as the external factor. In addition, the position of the silver ion or the conformation can be modulated also by variation of pH (variation of acidity of the surrounding environment).

According to the metal complex of a heterocyclic aromatic compound based on the present invention, the position of the silver ion can be modulated by the internal factor, such as transfer of electric charge, or the external factor, and the intrinsically unstable structure can be stabilized by the change of the position of the silver ion. Therefore, the metal complex of a heterocyclic aromatic compound based on the present invention can preferably function as a molecular device in technological fields.

In addition, the technological fields to which the metal complex is applied are not particularly limited. For example, use for a display utilizing variations in the color of emitted light may be mentioned as one example of the technological field, since the number of atoms (or the number of electrons) relating to the coordination ability can be regulated by the internal or external factor, and other examples of the technological fields include a molecular memory material utilizing the ability to change the structure, a refractive index modulation device, an analog switch, molecule recognition, an ion permeable film, etc.

Now, the present invention will be described more in detail by way of examples, but the invention is not limited to the examples.

EXAMPLE 1

An amorphous ITO film (sputtered at low temperature and enhanced in planarness, having a resistance of 200 Ω/□) was formed on a glass substrate measuring 10 mm by 30 mm with a thickness of 1.1 mm. Lead portions are formed at ends of the film, and the assembly was placed in a glass tank.

A mixed solution prepared by dissolving 0.04 mol/l of silver hexafluorophosphate and 0.10 mol/l of pyrrole in a propylene carbonate solution (containing 1% by weight of water) was obtained as an electrolytic solution in the glass tank. The solution was mixed well, and was left to stand for 72 hr.

A platinum substrate was disposed as a counter electrode in the solution, and an electric current of 2 mA was galvanostatically passed through the entire body of the solution from a driving circuit until the amount of electricity passed reached 50 $mC/cm^2$. As a result, an electrolytically polymerized film of a pyrrole-silver complex in an oxidized state (the metal complex of a heterocyclic aromatic compound based on the present invention) was formed on the ITO film. The polymerized film did not have a maximum absorption in the visible range, and was colorless (pale gray).

Next, the substrate was placed in a glass tank containing an electrolytic solution obtained by dissolving 1 mol/l of tetraammonium tetrafluoroborate in a propylene carbonate solution bubbled with nitrogen, and an electric current of −1 mA was galvanostatically passed through the solution until the amount of electricity passed reached 4 mC/cm², upon which the polymerized film turned light pink.

Subsequently, an electric current of −1 mA was further galvanostatically passed until the amount of electricity passed reached 4 mC/cm², upon which the polymerized film turned light green.

Next, an electric current of −1 mA was further galvanostatically passed until the amount of electricity passed reached 4 mC/cm², upon which the polymerized film turned light orange.

Subsequently, an electric current of −1 mA was further galvanostatically passed until the amount of electricity passed reached 4 mC/cm², upon which the polymerized film turned yellow.

In addition, when the polymerized film was left to stand in each colored state in a nitrogen atmosphere, the polymerized film retained the initial colored state even after several days.

COMPARATIVE EXAMPLE 1

A polymerized film was produced in the same manner as in Example 1, except that tetraammonium tetrafluoroborate was used in place of silver tetrafluorophosphate as an electrolyte in the glass tank. The polymerized film was deep reddish brown in color.

Next, the substrate was placed in a glass tank containing an electrolytic solution obtained by dissolving 1 mol/l of tetraammonium tetrafluoroborate in a propylene carbonate solution bubbled with nitrogen, and an electric current of −1 mA was galvanostatically passed through the electrolytic solution until the amount of electricity passed reached 4 mC/cm². Upon the passage of the current, the polymerized film momentarily turned light pink, but it immediately returned to the original deep reddish brown.

Subsequently, an electric current of −1 mA was further galvanostatically passed until the amount of electricity passed reached 4 mC/cm², upon which the polymerized film momentarily turned light pink, but it immediately returned to the original deep reddish brown.

Next, an electric current of −1 mA was further galvanostatically passed until the amount of electricity passed reached 4 mC/cm², upon which the polymerized film momentarily turned light pink, but it immediately returned to the original deep reddish brown.

Subsequently, an electric current of −1 mA was further galvanostatically passed until the amount of electricity passed reached 4 mC/cm², upon which the polymerized film abruptly turned yellow, but it turned deep reddish brown after 1 hr.

While the embodiments of the present invention and the example thereof have been described above, the embodiments and example can be modified variously based on the technical thought of the invention.

For example, while description has been made paying attention to pyrrole molecule and silver ion in the above embodiments and example, these are not limitative, and the kind of the acid to be used can easily be changed; in addition, the substituent group for changing the basicity may be selected as required.

Specifically, the 5-membered heterocyclic aromatic compound may contain a B (boron) or P (phosphorus) atom other than the N (nitrogen) atom, but it is necessary to secure such a structure that these atoms form a soft base, and, for example, it is preferable that such an atom is protonated or takes an sp3 hybrid orbital.

In addition, it is preferable that the transition metal ion is acidic. Examples of the transition metal ion includes ions of atoms belonging to Groups 1B to 5B of the periodic table. Specific examples include not only Ag but also Cu and Au, which can be used preferably. Further, there may be used such atoms that the number of electrons in the d-orbital becomes 10 upon ionization, and examples of such atoms include Zn, Cd, Hg, etc.

Besides, the metal complex of a heterocyclic aromatic compound based on the present invention preferably takes the form of a polymer with other molecule; for example, a compound may be formed in which the pyrrole molecule itself or other molecule is substituted for or added to a part of the complex.

According to the metal complex of a heterocyclic aromatic compound based on the present invention, the position of the central atom (namely, the number of atoms (or the number of electrons) relating to the coordination ability) can be regulated by the above-mentioned internal or external factor, and the intrinsically unstable structure can thereby be automatically stabilized. This means that a structural change of a derivative (inclusive of polymer) of the metal complex is effected depending on the change in the position of the central atom, whereby the structure is stabilized, and, particularly, the metal complex or the derivative thereof can preferably function as a molecular device in technological fields.

The invention claimed is:

1. A metal complex of a heterocyclic aromatic compound, comprising an acidic central atom comprised of a metal selected from the group consisting of Cu, Zn, Ag, Cd, Au and Hg, and basic ligands comprised of a 5-membered heterocyclic aromatic compound selected from the group consisting of pyrrole, pyrrole oligomers, pyrrolidone, thiophene, furan and combinations thereof wherein the position of said central atom can be changed by an internal factor or an external factor and wherein said internal factor is transfer of an electric charge and said external factor is application of an electric field or a change in acidity of the surrounding environment.

2. The metal complex of claim 1, wherein the 5-membered heterocyclic aromatic compound is pyrrolidine.

3. A metal complex of a heterocyclic aromatic compound as set forth in claim 2, wherein said central atom is comprised of an acidic transition metal ion.

4. A metal complex of a heterocyclic aromatic compound as set forth in claim 3, wherein said transition metal ion is a silver ion.

5. A metal complex of a heterocyclic aromatic compound as set forth in claim 1, which is a pyrrolidine-metal complex.

6. An ion permeable film capable of being used in a display, a molecular memory material, a refractive index modulation device, an analog switch, molecule recognition, or an ion permeable film which comprises the metal complex of claim 1.

7. The metal complex of claim 1, wherein the acidic central atom is a silver ion and the basic ligand is a pyrrolidine.

8. The metal complex of claim 6, wherein the position of the silver ion is changed by the transfer of an electric charge as said internal factor or by application of an electric field or a change in the acidity of the surrounding environment as said external factor.

9. An ITO film which comprises the metal complex of claim 1, wherein the position of the silver ion is changed by the transfer of a first electric charge to produce a first color and wherein the position of the silver ion is changed by the transfer of subsequent electric charge(s) to produce subsequent color(s) wherein the number of electric charges and number of colors is within the range of 1 to 5.

10. A metal complex of a heterocyclic compound as set forth in claim 1, wherein the basic ligands are comprised of 5-membered heterocyclic aromatic compound selected from the group consisting of pyrrole, thiophene, furan and combinations thereof.

11. The metal complex of claim 7, wherein the position of the silver ion is changed by the transfer by application of an electric field as said external factor.

12. A metal complex of a heterocyclic aromatic compound as set forth in claim 2, wherein the number of atoms of the 5-membered heterocyclic aromatic compound relating to the coordination ability on the ligand side can be regulated within range of 1 to 5 by the change in the position of said central atom.

* * * * *

UNITED STATES PATENT AND TRADEMARK OFFICE
CERTIFICATE OF CORRECTION

| | | |
|---|---|---|
| PATENT NO. | : 7,598,358 B2 | Page 1 of 1 |
| APPLICATION NO. | : 11/368793 | |
| DATED | : October 6, 2009 | |
| INVENTOR(S) | : Matsui et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this

Twenty-eighth Day of September, 2010

David J. Kappos
*Director of the United States Patent and Trademark Office*